(12) United States Patent
Kaur et al.

(10) Patent No.: US 8,075,931 B2
(45) Date of Patent: *Dec. 13, 2011

(54) **EXTRACTS OF *PHYLLANTHUS NIRURI***

(75) Inventors: Simarna Kaur, Green Brook, NJ (US);
Khalid Mahmood, Princeton, NJ (US);
Michael D. Southall, Lawrenceville, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/896,108

(22) Filed: Oct. 1, 2010

(65) Prior Publication Data

US 2011/0081308 A1    Apr. 7, 2011

Related U.S. Application Data

(63) Continuation-in-part of application No. 12/572,373, filed on Oct. 2, 2009.

(51) Int. Cl.
*A61K 36/00* (2006.01)
(52) U.S. Cl. .................................. 424/779; 424/725
(58) Field of Classification Search .................. None
See application file for complete search history.

(56) References Cited

U.S. PATENT DOCUMENTS

| | | | |
|---|---|---|---|
| 4,337,370 A | 6/1982 | Takisawa et al. | |
| 4,489,057 A | 12/1984 | Welters et al. | |
| 5,776,439 A | 7/1998 | Raspanti et al. | |
| 2005/0085454 A1 | 4/2005 | Ghosal | |
| 2007/0166255 A1 | 7/2007 | Gupta | |
| 2007/0196523 A1 | 8/2007 | Koganov | |
| 2008/0031833 A1* | 2/2008 | Oblong et al. | 424/59 |
| 2010/0322883 A1 | 12/2010 | Gohier et al. | |

FOREIGN PATENT DOCUMENTS

| | | | |
|---|---|---|---|
| EP | 1352640 | | 10/2003 |
| JP | 8012566 A | | 1/1996 |
| JP | 08176004 A | * | 7/1996 |
| JP | 8176004 A | | 7/1996 |
| JP | 1966176004 A | | 7/1996 |
| JP | 9087136 A | | 3/1997 |
| JP | 1997087136 A | | 3/1997 |
| JP | 2002308750 A | * | 10/2002 |
| JP | 2005008572 A | | 1/2005 |
| WO | WO 2009/067095 | | 5/2009 |

OTHER PUBLICATIONS

U.S. Appl. No. 12/572,373, Southall, et al.
Colipa Guideline: Guideline for the Colorimetric Determination of Skin Colour Typing and Prediction of the Minimal Erythemal Dose (MED) Without UV Exposure, published in 2007, p. 1-11.
Martin et al., "Parthenolide-depleted Feverfew (*Tanacetum parthenium*) protects skin from UV irradiation and external aggression", Arch Dermatol Res. (2008) 300:69-80.
www.rain-tree.com, "Database File for: Chanca Piedra (*Phyllanthus niruri*)" reprinted from Taylor, "The Healing Power of Rainforest Herbs", (2005).
Chaudhuri RK, "Emblica Cascading Antioxidant: A Novel Natural Skin Care Ingredient", Skin Pharmacol Appl Skin Physiol. Sep.-Oct. 2002; 15(5):374-80.
Barros, M.E. et al., "Effects of an aqueous extract from *Phyllantus niruri* on calcium oxalate crystallization in vitro", Urol Res. Feb. 2003, 30(6):374-9.
Ogata, T. et al., "HIV-1 reverse transcriptase inhibitor from *Phyllantus niruri*", AIDS Res Hum Retroviruses Nov. 1992; 8(11): 1937-44.
Qian-Cutrone, J. et al., "Niruriside, a new HIV REV/RRE binding inhibitor from *Phyllanthus niruri*", J Nat Prod Feb. 1996; 59(2):196-9.
Kiemer, A.K., et al., "*Phyllanthus amarus* has anti-inflammatory potential by inhibition of iNOS, COX-2 and cytokines via the NF-kappaB pathway", J Hepatol. Mar. 2003; 38(3):289-97.
Bagalkotkar, G., "Phytochemicals from *Phyllanthus niruri* Linn. and their pharmacological properties: a review", J Pharm Pharmacol. 2006; 58(12):1559-70.
Kassuya et al., "Antiinflammatory and antiallodynic actions of the lignan niranthin isolated from *Phyllanthus amarus*," European Journal of Pharmacology, Elsevier BV, NL, vol. 546, No. 1-3, Sep. 28, 2006, pp. 182-188, XP005646245.
Kassuya et al., "Anti-Inflammatory Properties of Extracts, Fractions and Lignans Isolated from *Phyllanthus amarus*," Planta Medica, Thieme Verlag, DE, vol. 71, No. 8, Aug. 1, 2005, pp. 721-726, XP009145102.
Database WPI, Week 199612, Thomson Scientific, London, GB; AN 1996-112627, XP002625249.
Database WPI, Week 199723, Thomson Scientific, London, GB; AN 1997-255417, XP002625250.
Database WPI, Week 199637, Thomson Scientific, London, GB; AN 1996-368117, XP002625251.
PCT International Search Report for International Application No. PCT/US2010/051089 dated Mar. 14, 2011.

* cited by examiner

*Primary Examiner* — Christopher R. Tate
*Assistant Examiner* — Deborah A. Davis

(57) ABSTRACT

A method of making a low molecular weight fraction of *Phyllanthus niruri* is provided. Such low molecular weight fraction is particularly useful for treating the skin, for example skin in need of treatment for signs of aging, for reducing inflammation, or for skin lightening.

5 Claims, No Drawings

EXTRACTS OF *PHYLLANTHUS NIRURI*

CROSS REFERENCE TO RELATED APPLICATIONS

This application is a continuation-in-part of U.S. Ser. No. 12/572,373 filed Oct. 2, 2009. The complete disclosure of the aforementioned related U.S. patent application is hereby incorporated herein by reference for all purposes.

FIELD OF THE INVENTION

The present invention relates to compositions comprising, as well as methods of making and using, extracts of *Phyllanthus niruri*. The compositions are useful for example for improving the appearance of skin, for example improving the signs of skin aging, treating inflammation, and lightening the skin.

BACKGROUND OF THE INVENTION

Aging of the skin can adversely affect elasticity and strength of the skin through changes in the two main constituents of the dermal extracellular matrix, the fibrous proteins collagen and elastin. For example, elastin is a large fibrous protein formed by the crosslinking of elastin precursor protein molecules (e.g., tropoelastin) into spiral filaments. The spiral filaments consist of peptidic chains that are capable of extending and then resuming their original shape.

Compositions comprising *Phyllanthus niruri* to treat the skin are known in the art. However, the inventors have recognized that not all extracts of *Phyllanthus niruri* perform equivalently in promoting tropoelastin and collagen formation. The inventors have surprisingly found that water-extractable, low molecular weight fractions of *Phyllanthus niruri* have significantly better activity than other extracts of *Phyllanthus niruri* for inhibiting collagenase, promoting tropoelastin, and promoting collagen formation.

It has also been discovered that such low molecular weight fractions of *Phyllanthus niruri* are also highly useful for skin lightening.

It has further been discovered that low molecular weight fractions of *Phyllanthus niruri* provide beneficial anti-inflammatory effects.

SUMMARY OF THE INVENTION

The invention relates to a composition consisting essentially of a low molecular weight fraction of *Phyllanthus niruri* substantially free of molecular species having a molecular weight of greater than about 100,000 daltons.

The invention also relates to a topical formulation comprising a cosmetically acceptable topical carrier and a composition consisting essentially of a low molecular weight fraction of *Phyllanthus niruri* substantially free of molecular species having a molecular weight of greater than about 100,000 daltons, as well as a method of treating a sign of skin aging by topically applying such topical formulation to the skin.

The invention further relates to a method of making a low molecular weight fraction of *Phyllanthus niruri*, said method comprising: contacting *Phyllanthus niruri* with a solvent comprising water for a time period sufficient to form a water extract of *Phyllanthus niruri*; and isolating a low molecular weight fraction from said water extract of *Phyllanthus niruri*.

In another aspect, the invention is directed to methods of lightening the skin comprising the step of applying to skin in need of skin lightening treatment a low molecular weight fraction of *Phyllanthus niruri* substantially free of molecular species having a molecular weight of greater than about 100,000 daltons.

In another aspect, the invention is directed to methods of improving a sign of skin aging comprising the step of applying to skin in need of improving the signs of aging a low molecular weight fraction of *Phyllanthus niruri* substantially free of molecular species having a molecular weight of greater than about 100,000 daltons.

The invention is also directed to methods of reducing skin inflammation comprising the step of applying to a skin in need of reducing skin inflammation a low molecular weight fraction of *Phyllanthus niruri* substantially free of molecular species having a molecular weight of greater than about 100,000 daltons.

Other features and advantages of the present invention will be apparent from the detailed description of the invention and from the claims.

DETAILED DESCRIPTION OF PREFERRED EMBODIMENTS

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

As used herein, "signs of skin aging" includes the presence of lines and wrinkles, loss of elasticity, uneven skin, blotchiness, and age spots.

As used herein, "treating" refers to mitigating, reducing, preventing, improving, or eliminating the presence or appearance of a condition or disease.

As used herein, "wrinkle" includes fine lines, fine wrinkles, or coarse wrinkles. Examples of wrinkles include, but are not limited to, fine lines around the eyes (e.g., "crow's feet"), forehead and cheeks, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of the application of products, such as cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "age spots" means a condition of the skin associated with discrete pigmentation, e.g., small areas of darker pigmentation that may develop on the face as well as the hands.

As used herein, "treatment of external aggressions in skin" means the reduction or prevention of the damage from external aggressions in skin. Examples of external aggressions include, but are not limited to, damage to the skin from the use or cleansers (e.g., topical cleansers containing surfactants), make-up, shaving as well as environmental damage such as from UV light (e.g., sundamage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, "skin in need of reducing skin inflammation" means a skin exhibiting redness or erythema, edema. In certain other embodiments, "skin in need of reducing skin inflammation" refers to skin that is particularly reactive or sensitive to external elements. External elements include, but are not limited to, sun rays (UV, visible, IR), microorganisms, atmospheric pollutants such as ozone, exhaust pollutants, chlorine and chlorine generating compounds, cigarette smoke, cold temperature, heat. Inflammatory disorders and related conditions which may be treated or prevented by use of the compositions of this invention include, but are not limited to the following: arthritis, bronchitis, contact dermatitis, atophic dermatitis, psoriasis, seborrheic dermatitis, eczema, allergic dermatitis, polymorphous light eruptions, inflammatory dermatoses, folliculitis, alopecia, poison ivy, insect bites, acne inflammation, irritation induced by extrinsic factors including, but not limited to, chemicals, trauma, pollutants (such as cigarette smoke) and sun exposure, secondary conditions resulting from inflammation including but not limited to xerosis, hyperkeratosis, pruritus, postinflammatory hyperpigmentation, scarring and the like. Preferably, the inflammatory disorders and related conditions which may be treated or prevented using the methods of the invention are arthritis, inflammatory dermatoses, contact dermatitis, allergic dermatitis, atopic dermatitis, polymorphous light eruptions, irritation, including erythema induced by extrinsic factors, acne inflammation, psoriasis, seborrheic dermatitis, eczema, poison ivy, insect bites, folliculitis, alopecia, and secondary conditions and the like.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

As used herein, "improving the tone" means the lightening of the appearance of the skin (e.g., lightening pigmented marks or lesions, reducing skin sallowness, and/or evening the color of the skin).

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the user, the severity of the condition being treated/prevented, the duration of the treatment, the nature of other treatments, the specific compound or product/composition employed, the particular cosmetically-acceptable carrier utilized, and like factors.

It is believed that one skilled in the art can, based upon the description herein, utilize the present invention to its fullest extent. The following specific embodiments are to be construed as merely illustrative, and not limitative of the remainder of the disclosure in any way whatsoever.

As used herein, *Phyllanthus niruri* includes both *Phyllanthus niruri* and *Phyllanthus amarus*.

*Phyllanthus niruri* may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nev.

According to a first step of the method of the invention, *Phyllanthus niruri* (optionally prepared as discussed above) is contacted with a solvent comprising water for a time period sufficient to form a water extract of the *Phyllanthus niruri*. The solvent comprises water, preferably at least about 50% water, more preferably at least about 75% water, and most preferably at least about 90% water.

In one embodiment, the solvent comprises less than about 10% of organic solvents (e.g., ethanol, methanol, and the like). In a preferred embodiment, the solvent includes less than about 5% of organic solvents. In a further preferred embodiment, the solvent includes less than about 1% of organic solvents. In yet another preferred embodiment, the solvent includes no organic solvent. If organic solvent is included in the solvent, refluxing the resulting liquid phase in a temperature range from 60 to 100° C. may be required to remove the organic solvent.

Accordingly, in certain embodiments of the invention, the molecular species in the water extract of *Phyllanthus niruri* are water extractable. As used herein, "water extractable" means capable of being extracted by contacting with a solvent that includes at least about 50% water, more preferably at least about 75% water, and most preferably at least about 90% water.

The ratio of the mass of *Phyllanthus niruri* to solvent may be varied. In one embodiment the ratio of the mass of *Phyllanthus niruri* to solvent is from about 1:2 to about 1:50, preferably from about 1:3 to about 1:20, even more preferably from about 1:4 to about 1:12.

To enhance extraction, the *Phyllanthus niruri* may be sonicated in the solvent. Alternatively, or in addition, the solvent may be heated, such as to a temperature between about 30° C. and about 70° C., preferably from about 40° C. to about 65° C., more preferably from about 40° C. to about 65° C.

The *Phyllanthus niruri* and the solvent are preferably contacted for a time period of at least about 5 minutes, preferably from about 10 minutes to about 6 hours, more preferably from about 10 minutes to about 60 minutes, most preferably about 30 minutes.

The water extract is desirably separated by filtration using conventional filtration techniques, such as through a Buchner funnel using a Whatman filter paper. The resulting water extract of *Phyllanthus niruri* is then available for additional processing as follows.

According to a second step of the method of the invention, a low molecular weight fraction of the water extract of *Phyllanthus niruri* is then isolated. A suitable means for isolating the low molecular weight fraction is by gel filtration, i.e., gel permeation chromatography (GPC) employing a membrane that will selectively pass only those molecular species above or below a particular molecular weight cutoff.

As is well understood by those skilled in the art, a GPC column is first packed with a non-ionic crosslinked polymer resin. The resin is thoroughly washed, such as with the following liquids, in sequence: 1 liter of water, 1 liter of water-methanol, and 1 liter of methanol, followed by conditioning with water. The water extract of *Phyllanthus niruri* is the passed through for example a 100 kD (100,000 dalton) membrane using a Spectrum MiniKros to concentrate and separate molecules having molecular weights less than 100,000 dalton. The portion that passes through the membrane is isolated as the low molecular weight fraction of *Phyllanthus niruri*. The remaining portion of the water extract may optionally and preferably be discarded.

In this manner, a composition is made consisting essentially of a low molecular weight fraction of *Phyllanthus niruri* that is substantially free of molecular species having a molecular weight of greater than about 100,000 daltons. As used herein, "substantially free of molecular species having a molecular weight of greater than about 100,000 daltons" means such composition contains less than about 10% by weight, preferably less than about 5% by weight, more preferably less than about 2% by weight, even more preferably less than about 1% by weight, even more preferably less than about 0.5% by weight, and even more preferably less than about 0.1% by weight of molecular species having molecular weights greater than about 100,000 daltons. As one skilled in the art will readily appreciate, the concentration of molecular species having molecular weights greater than about 100,000 daltons in the low molecular weight fraction of *Phyllanthus niruri* may be adjusted by, for example, adjusting the cutoff molecular weights allowed through the membrane of the GPC.

The solvent (e.g., water) may or may not be dried off or evaporated. It should be noted that the percentages of molecular species having particular molecular weight ranges described herein are calculated exclusive of any residual solvent. In a preferred embodiment, the method of the invention further includes at least partially (or completely) removing remaining solvent in the low molecular weight fraction, such as by freeze drying.

Topical Formulations

The composition consisting essentially of a low molecular weight fraction of *Phyllanthus niruri* may be combined with one or more cosmetically acceptable topical carriers to form a topical formulation suitable for use on skin.

As used herein, "cosmetically acceptable" means suitable for use in contact with (human) tissues (e.g., the skin) without undue toxicity, incompatibility, instability, irritation, allergic response, and the like, commensurate with a reasonable benefit/risk ratio.

Suitable topical carriers include, but are not limited to, water, ethanol, isopropanol, 1,2-propanediol, glycerin, benzyl alcohol, dimethylisosorbide, triacetin, glycol ethers, propylene glycol, polyethylene glycol (PEG), and combinations thereof. Particularly preferred carriers include PEG having an average molecular weight between about 200 and about 400, castor oil, triacetin, dimethylisosorbide, ethanol, and water, and combinations thereof.

Various compounds may be added to the topical formulation to alter osmolarity and/or pH to acceptable levels. These include, but are not limited to, mannitol, sucrose, calcium chloride, sodium chloride, sodium phosphate monobasic, sodium phosphate dibasic, sodium hydroxide, and hydrochloric acid.

The topical formulations may be made into a wide variety of cosmetic articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like.

These product types may contain several types of cosmetically acceptable topical carriers including, but not limited to solutions, suspensions, emulsions such as microemulsions and nanoemulsions, gels, solids and liposomes. Other carriers can be formulated by those of ordinary skill in the art. In order to facilitate the formulation of a suitable carrier, one may include any of various functional ingredients. For example, one may include any of a number of emollients, humectants, pH adjusters, sequesterants, emulsifiers, wetting agents, thickeners, polymers, preservatives, colorants, fragrances, and other ingredients commonly used in personal care and cosmetic products. The pH chosen is not critical, but may be in a range, for example that is from about 4 to about 8, such as from about 5 to about 7.

The cosmetically acceptable topical carrier may constitute from about 50% to about 99.99%, by weight, of the topical formulation, more preferably from about 80% to about 95%, by weight, of the topical formulation. In a particularly preferred embodiment, the topical formulation includes at least about 25% by weight water, more preferably at least about 50% by weight water.

In one embodiment, the topical formulation may further contain one or more additional cosmetically active agent(s) as well as the above-mentioned components. What is meant by a "cosmetically active agent" is a compound, which may be a synthetic compound or a compound extracted, isolated, purified or concentrated from a natural source, or a natural extract containing a mixture of compounds, that has a cosmetic or therapeutic effect on the tissue, including, but not limited to: anti-microbial agents such as anti-yeast, anti-fungal, and anti-bacterial agents, anti-inflammatory agents, anti-aging agents, depigmentaion agents, anti-parasite agents, antioxidants, keratolytic agents, nutrients, vitamins, minerals, energy enhancers, sunscreens and the like.

Examples of vitamins that may be constituents of the compositions of this invention include, but are not limited to, vitamin A, vitamin Bs such as vitamin B3, vitamin B5, vitamin B7 and vitamin B12, vitamin C, vitamin K, vitamin E such as alpha, gamma or delta-tocopherol, and their derivatives (such as salts and esters) and mixtures thereof.

Examples of antioxidants which may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention include, but are not limited to, extracts containing flavinoid, isoflavinoid, and their derivatives such as genistein and diadzein (e.g., such as soy and clover extracts, extracts containing resveratrol and the like. The one or more additional cosmetically active agent(s) may be present in any suitable concentration, such as, for example from about 0.1% to about 10% by weight.

Examples of anti-aging agents that which may be utilized include, but are not limited to, retinoids (e.g., retinol and retinyl palmitate) and amine compounds of formula I or formula II, shown below:

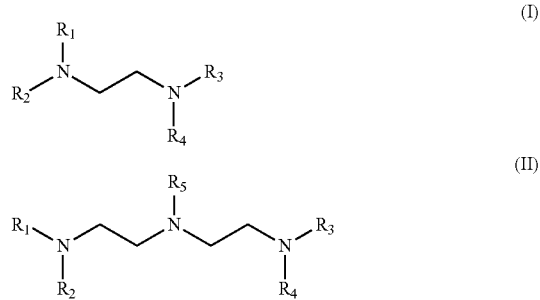

wherein $R_1$, $R_2$, $R_3$, $R_4$, and $R_5$ independently are selected from the group consisting of hydrogen, $C_1$-$C_6$ alkyl, and $C_1$-$C_6$ hydroxyalkyl; or a cosmetically-acceptable salt thereof.

Examples of preferred amine compounds of formula I include, but are not limited to, N,N,N',N'-tetrakis(2-hydroxypropyl)ethylenediamine (THPED), N,N,N',N'-tetrakis(2-hydroxyethyl)ethylene diamine (THEED), N,N,N',N'-tet- ramethylethylene diamine (TEMED), enantiomers thereof, diastereoisomers thereof, and cosmetically-acceptable salts thereof.

Other examples of anti-aging actives include: copper containing peptides; vitamins such as vitamin E, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, pyruvic acid; beta hydroxy acids such as beta-hydroxybutyric acid, beta-phenyl-lactic acid, beta-phenylpyruvic acid; polyphenolics; botanical extracts such as green tea, soy products, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Examples of suitable depigmentation agents include, but are not limited to soy products, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinoids, Kojic acid, soy products, and hydroquinone being particularly suitable examples.

In one embodiment, the topical formulation comprises one or more additional skin lightening agents. Examples of additional skin lightening agents include phenylethyl resorcinol, 4-hexyl resorcinol, α-arbutin, kojic acid, nivitol, ascorbyl-2-glucoside, soy extract, niacinamide, and combinations of two or more thereof.

Examples of sunscreens include UV-A and UV-B absorbing sunscreens. UV-A absorbing sunscreens include tetrahydroxybenzophenones; dicarboxydihydroxybenzophenones and alkane ester or acid halide derivatives thereof; dihydroxy-, dicarboxy-, and hydroxycarboxydibenzoylmethanes and alkane ester or acid halide derivatives thereof; dihydroxy-, dicarboxy-, and hydroxycarboxystilbenes and alkane ester or acid halide derivatives thereof; bis(hydroxystyrenyl)benzenes; bis(carboxystyrenyl)benzenes and alkane ester or acid halide derivatives thereof; dihydroxy-, dicarboxy, and hydroxycarboxycarotenes and alkane ester or acid halide derivatives thereof; 2 cyano-3,3-diphenyl acrylic acid, 2-ethyl hexyl ester; and any suitably functionalized species capable of copolymerization within the polymer chain capable of absorbing ultraviolet light in the 320-400 nm range.

In one embodiment, the sunscreen is a UV-absorbing triazole and/or a UV-absorbing benzoylmethane, such as methylene bis-benzotriazolyl tetramethylbutylphenol (TINSORB M, Ciba Specialty Chemicals Corporation, Greensboro, N.C., USA). Other UV-absorbing dibenzoylmethanes include 2-(4-diethyl amino-2 hydroxybenzol)-benzoic acid hexylkester, commercially available as UVINUL A Plus from BASF of Parsippany, N.J.

UV-absorbing dibenzoylmethanes are disclosed in U.S. Pat. No. 4,489,057 and include, but are not limited to, 4-(1,1-dimethylethyl)-4'-methoxydibenzoylmethane (avobenzone and sold as PARSOL 1789, Roche Vitamins and Fine Chemicals, Nutley, N.J., USA), 2-2-methyldibenzoylmethane, 4-methyl-dibenzoylmethane, 4-isopropyldibenzoylmethane, 4-tert-butyldibenzoylmethane, 4-tert-butyl-4'-methoxydibenzoylmethane, 2,4-dimethylbenzoylmethane, 2,5-dimethylbenzoylmethane, 4,4'-diisopropylbenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

Examples of suitable UV-B absorbing sunscreens include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; and other suitably functionalized species capable of copolymerization within the polymer chain.

Particularly suitable UV-B absorbing moieties include UV-absorbing benzophenones and UV-absorbing diphenylcyanoacrylate derivatives. Examples of benzophenone derivatives include those known in the art to provide protection of the skin from UV radiation, for example, such as taught by U.S. Pat. No. 5,776,439. Preferred compounds include 2-hydroxy-4-methoxybenzophenone (oxybenzone) and 2-2'dihyroxy-4-methoxybenzophenone ("dioxybenzone") and diethylamine hydroxybenzoyl hexyl benzoate ("hydroxybenzophenone"). Examples of diphenylcyanoacrylate derivatives include 2-ethylhexyl 2-cyano-3,3-diphenyl-2-propenoate (octocrylene).

While the sunscreens may be "organic sunscreens" (also known as UV filters), such as those described above that absorb radiation in the UV, in certain embodiments, the formulation may also include "physical" sunscreens, generally water insoluble particulate compounds that scatter UV radiation. Examples of such physical sunscreens include zinc oxide and titanium oxide.

In one embodiment the topical formulation comprises a sunscreen selected from the group consisting of phenylbenzimidazole sulfonic acid, methylene bis-benzotriazolyl tetramethylbutylphenol, ethylhexyl salicylate, octocrylene, benzophenone-3, ethylhexyl triazone, avobenzone, homosalate, bis-ethylhexyloxyphenol methoxyphenyl triazine, and mixtures thereof.

In one embodiment, the topical formulation comprises one or more additional anti-inflammatory agents. Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extract of *Paulownia tomentosa* wood, and extracts and materials derived from the following:
Phellodendron Amurense Cortex Extract (PCE)
Non-Denatured Soy (*Glycine max*)
Feverfew (*Tanacetum parthenium*)
Ginger (*Zingiber officinale*)
Ginko (*Ginko Biloba*)
Madecassoside (*Centella asiatica* extract ingredient)
Cotinus (*Cotinus coggygria*)
Butterbur Extract (*Petasites hybridus*)
Goji Berry (*Lycium barbarum*)
Milk Thistle Extract (*Silybum marianum*)
Honeysuckle (*Lonicera japonica*)
Basalm of Peru (*Myroxylon pereirae*)
Sage (*Salvia officinalis*)
Cranberry Extract (*Vaccinium oxycoccos*)
Amaranth Oil (*Amaranthus cruentus*)
Pomegranate (*Punica granatum*)
Yerbe Mate (*Ilex paraguariensis* Leaf Extract)
White Lily Flower Extract (*Lilium Candidum*)
Olive Leaf Extract (*Olea europaea*)
Phloretin (apple extract)
Oat Flour (*Aveena Sativa*)
Lifenol (Hops: *Humulus lupulus*) Extract
Bugrane P (*Ononis spinosa*)
Licochalcone (Licorice: Glycyrrhiza inflate extract ingredient)
Symrelief (Bisabolol and Ginger extract)
and combinations of two or more thereof, and the like.

Resorcinol is a dihydroxy phenol compound (i.e., 1,3 dihydroxybenzene) having by the following structure:

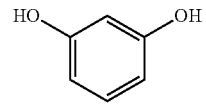

As used herein, "substituted resorcinol" means resorcinol comprising at least one substituent in the 2, 4, 5, or 6 position. Thus, the substituted resorcinol may have as few as one and as many as four substituents. Positions 1 and 3 of the substituted resorcinol comprise —OH groups, as shown above.

In embodiments wherein substituted resorcinol is used for anti-inflammation, it is highly preferred that all of the substituents of the substituted resorcinol are free of phenyl (—C6H5 aromatic) moieties. In certain embodiments, all of the substituents are free of aromatic moieties (with or without heteroatoms). In certain such embodiments, it is preferred that all of the substituents of the substituted resorcinol are free of ketone functionalities (carbonyls bonded to two other carbon atoms). In certain other such embodiments, all of the substituents of the substituted resorcinol are free of both phenyl functionalities and ketone functionalities. In certain other such embodiments, the substituted resorcinol comprises at least one substituent comprising 5 to 11 carbon atoms, preferably 5 to 10 carbon atoms, more preferably 5 to 9 carbon atoms, most preferably 5 to 8 carbon atoms. In certain other such embodiments, at least one substituent comprises an alkyl group, such as one having the number of carbon atoms described above. The alkyl group is preferably unsaturated.

In certain embodiments, the 4 position of the resorcinol is substituted, and, in certain embodiments, only the 4 position is substituted. In another embodiment, the 4 position is substituted with an alkyl group. In certain preferred embodiments, the substituted resorcinol comprises a single substituent at the 4 position that comprises an alkyl group. In certain other preferred embodiments, the substituted resorcinol comprises a single substituent at the 4 position that consists of an alkyl group directly bonded to the benzene ring.

Particularly suitable substituted resorcinols for anti-inflammation agents include 4-hexyl resorcinol and 4-octylresorcinol, particularly 4-hexyl resorcinol. The structures of 4-hexylresorcinol and 4-octylresorcinol are shown below:

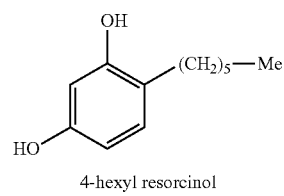

4-hexyl resorcinol

-continued

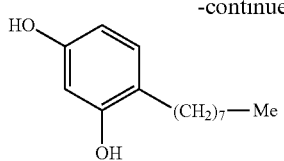

4-octylresorcinol

4-Hexyl resorcinol is commercially available as "SYNOVEA HR" from Sytheon of Lincoln Park, N.J. 4-Octylresorcinol is commercially available from City Chemical LLC of West Haven, Conn.

In certain embodiments, the substituted resorcinol comprises at least two substituents in the 2, 4, 5, or 6 positions. Such substituents may optionally be linked to form a ring, such as a cyclic aliphatic hydrocarbon optionally comprising heteroatoms such as sulfur or oxygen. Such a linked substituent may comprise 5 to 10 carbon atoms, e.g., 8 to 10 carbon atoms, and optionally include 1 to 3 heteroatoms. Examples of suitable substituted resorcinols comprising cyclic aliphatic substituents joining the 2 and 3 positions include Zearalanone and β-Zearalanol:

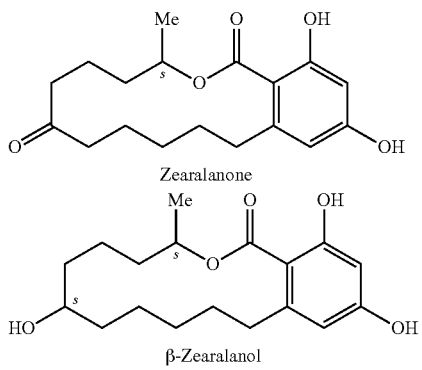

Zearalanone

β-Zearalanol

Zearalanone and β-Zearalanol are commercially available from Sigma Chemicals of St. Louis, Mo.

In certain other embodiments, the substituted resorcinol comprises halide-containing and/or nitroso-containing substituents. Suitable examples contain —Cl or —N═O bonded directly to the benzene ring. These substituents may exist for example in the 2 and 4, 2 and 6, or 4 and 6 positions. An example of a dihalide-substituted resorcinol is 2,6-dichlororesorcinol. An example of a dinitroso-substituted resorcinol is 2,4-dinitrososorcinol:

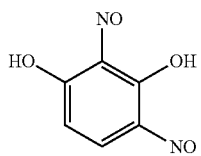

2,4-dinitrososorcinol 2,6-Dichlororesorcinol and 2,4-Dinitrososorcinol are available from City Chemical LLC of West Haven, Conn.

Substituted resorcinols are prepared by means known in the art, for example, using techniques described in U.S. Pat. No. 4,337,370, the contents of which are incorporated herein by reference.

The substituted resorcinols may have any suitable molecular weight. In certain embodiments, the molecular weight of the substituted resorcinol ranges between about 175 and about 300.

By "extracts of feverfew," it is meant extracts of the plant "*Tanacetum parthenium*," such as may be produced according to the details set for the in US Patent Application Publication No. 2007/0196523, entitled "PARTHENOLIDE FREE BIOACTIVE INGREDIENTS FROM FEVERFEW (*TANACETUM PARTHENIUM*) AND PROCESSES FOR THEIR PRODUCTION." One particularly suitable feverfew extract is commercially available as about 20% active feverfew, from Integrated Botanical Technologies of Ossining, N.Y.

*Paulownia* is a genus of plants native to Asia which has spread gradually to Europe and the USA. In Japan, *Paulownia* is called kiri which refers specifically to one species, *Paulownia tomentosa*, also called "Princess Tree." Other names which are commonly used are "empress tree," "Foxglove Tree," "Royal *Paulownia*," "Pao tong" (in China) and "Odong-Namoo" (in Korea). The scientific name is "*Paulownia tomentosa*" with a number of synonyms reported in various literature, i.e. "*Paulownia imperialis*," "*Paulownia recurva*," and "*Bignonia tomentosa*." *Paulownia tomentosa* belongs to the family "Paulowniaceae" sometimes referred to as "Scrophulariaceae." The United States Department of Agriculture (plants.USDA.gov) Plant database identifies Princess tree by a unique symbol "PATO2," with *Paulownia tomentosa* and *Paulownia imperialis* as synonym names.

Any suitable extracts of *Paulownia tomentosa* wood may be used. In general, the wood of the *Paulownia tomentosa* tree includes wood from the stem, branches, or a combination of both. Suitable extracts of *Paulownia tomentosa* wood may be derived from wood chips, wood dusts and/or small cuttings, and the like.

Compositions of the present invention may include a cosmetically effective amount of one or more additional anti-inflammatory compounds. The compositions preferably include, on an active basis, from about 0.1% to about 10%, more preferably from about 0.5% to about 5%, of the additional anti-inflammatory compound.

The low molecular weight fraction of *Phyllanthus niruri*, cosmetically acceptable topical carrier and optional additional cosmetically active agents may be combined in any proportion to form a topical formulation suitable for topical use. In one embodiment of the invention, the topical formulation comprises at least about 0.0001% by weight, for example at least about 0.1% by weight, of the low molecular weight fraction of *Phyllanthus niruri*. In certain embodiments, the topical formulation comprises at least about 0.5%, say about 0.75% to about 2.0% by weight, or up to and including about 5.0% by weight, of the low molecular weight fraction of *Phyllanthus niruri*.

For embodiments comprising skin lightening uses of the composition or formulation, a "skin lightening effective amount" of means an amount of extract that is effective to achieve a ΔL value that is greater than zero in the Skin Epidermal Equivalents Model as a skin Lightening Test (ΔL) as described in Example IX below. In certain preferred embodiments, the skin lightening effective amount is an amount effective to achieve a ΔL value of about 1 or greater.

For embodiments of the present invention related to uses of the compositions for reducing inflammation, an "effective amount for reducing inflammation" means an amount that provides a percent inhibition of skin inflammation (IL-8), measured in accord with the Anti-Inflammatory effects on Release of UV-Induced Pro-inflammatory mediators on Reconstituted Epidermis procedure for IL-8 of Example VI below, that is greater than zero. In certain preferred embodiments, the effective amount for improving a sign of aging is an amount that provides a percent inhibition of skin inflammation (IL-8), measured in accord with the Anti-Inflammatory effects on Release of UV-Induced Pro-inflammatory mediators on Reconstituted Epidermis procedure for IL-8 of Example VI below, that is about 10% or greater.

Topical formulations comprising compositions consisting essentially of the low molecular weight fraction of *Phyllanthus niruri* may be topically applied to mammalian skin that is in need of treatment for one or more signs of skin aging as described above. In one embodiment, the topical formulations are applied to skin in need of treatment for lines and wrinkles and/or loss of elasticity. In another embodiment, the topical formulations are applied to skin in need of reducing skin inflammation. In another embodiment, the topical formulations are used to treat external aggressions in skin (e.g., for use after sun exposure). In a further embodiment, the topical formulations are used to lighten skin in need of skin lightening. The topical formulations may be applied to the skin in need of such treatment according to a suitable treatment regimen, e.g., every month, every week, every other day, every day, twice a day, or the like.

In certain embodiments, topical formulations of the present invention may also be useful for treating other need states associated with skin. For example, the topical formulations may be useful for treating post-inflammatory depigmentation/hyperpigmentation, for reducing pore size, acne treatment, and for scar mitigation. In certain other embodiments, the topical formulations may be applied simultaneously with or within several hours of a mechanical or physical exfoliant such as a microdermabrasion treatment, or with a chemical exfoliant or keratolytic agent such as salicylic acid. In certain other embodiments, the topical formulations are applied to mucosa or other tissue such as vaginal, oral, or ocular tissue. In certain other embodiments, the topical formulations are applied to mild wounds or post-surgical sites to facilitate healing, to insect bites, to poison ivy or similar skin conditions, or in general to mitigate itch. In certain other embodiments, the topical formulations are applied to mitigate skin irritations. Such irritations may be of external origin, i.e., caused by ingredients in skin care and cosmetic products such as retinoids and their derivatives, benzoyl peroxide, alpha-hydroxy acids and derivatives thereof, salicylic acid, surfactants, natural plant extracts, sunscreen actives, urea, and preservatives etc. Such irritations may be of other external origin such as the sun, wind, or shaving. Irritation may also be caused by diseases and conditions such as acne, rosacea, atopic dermatitis, and other disease states.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example I

Four different solvent extracts of *Phyllanthus niruri* were prepared. *Phyllanthus niruri* (Raintree Nutrition, Inc., Carson City, Nev.) was extracted separately in each of methanol, hexane, ethyl acetate, and water by sonicating for 30 min at 60° C. No molecular weight fractionation was performed on the solvent extracts, each of which was recovered by filtration though a Buchner funnel using a Whatman filter paper. Volatiles were evaporated by freeze drying.

Example II

Enzyme activities of the solvent extracts of *Phyllanthus niruri* of Example I were evaluated for collagenase inhibition using the EnzChek Collagenase assay. The ability of each solvent extract to inhibit the activity of the collagenase Type IV enzyme from *Clostridium histolyticum* on the DQ elastin from pig skin (substrate) was fluorometrically assayed in a Microplate reader. The IC50 values are indicated below in Table 1.

TABLE 1

| Extract | IC50 value for the Collagenase Enzyme |
| --- | --- |
| Methanol Extract Of *Phyllanthus niruri* | >500 ug/ml |
| Hexane Extract Of *Phyllanthus niruri* | 223.1 ug/ml |
| Ethyl acetate Extract Of *Phyllanthus niruri* | 334.6 ug/ml |
| Water Extract Of *Phyllanthus niruri* | 27.6 ug/ml |

The water extract of *Phyllanthus niruri* provided a substantially greater collagenase inhibition than the methanol, hexane, or ethyl acetate extracts.

Example III 51.2 g of *Phyllanthus niruri* (Raintree Nutrition, Inc., Carson City, Nev.) was extracted with 320 mL of water by sonicating for 30 min at 60° C. The liquid phase was removed by filtration though a Buchner funnel using a Whatman filter paper.

A gel fractionation column was packed with 60 g of XAD-4 resin (non-ionic crosslinked polymer resin). The resin was thoroughly washed in sequence with water (1 L volume), water-methanol (50:50, 1 L), methanol (1 L) and conditioned with water prior to loading. The above prepared water extract was passed through a 100 kD membrane using Spectrum MiniKros (Spectrum Laboratories, Inc., Rancho Dominguez, Calif.) to concentrate and separate small molecules, yielding a low molecular weight fraction of the water extract.

A comparative water extract of *Phyllanthus niruri* was not fractionated (i.e., it contained both low molecular weight and high molecular weight species).

Volatiles were evaporated by freeze drying.

Enzyme activities of both water extracts were evaluated for collagenase enzyme activity. The IC50 values are indicated in Table 2 below.

TABLE 2

| Extract | IC50 value for the Collagenase Enzyme |
| --- | --- |
| *Phyllanthus niruri* Water Extract | 27.6 ug/ml |
| Low Molecular Weight fraction of *Phyllanthus niruri* Water Extract | 7.8 ug/ml |

These results demonstrate that the low molecular weight fraction of the *Phyllanthus niruri* water extract provides a substantially greater, i.e., more than three times greater, collagenase inhibition than *Phyllanthus niruri* water extract containing both high and low molecular weight molecular species.

Example IV 51.2 g of *Phyllanthus niruri* (Raintree Nutrition, Inc., Carson City, Nev.) was extracted with 320 mL of water by sonicating for 30 min at 60° C. The liquid phase was removed by filtration though a Buchner funnel using a Whatman filter paper.

A gel fractionation column was packed with 60 g of XAD-4 resin (non-ionic crosslinked polymer resin). The resin was thoroughly washed in sequence with water (1 L volume), water-methanol (50:50, 1 L), methanol (1 L) and conditioned with water prior to loading. The above prepared water extract was passed through a 100 kD membrane using Spectrum MiniKros (Spectrum Laboratories, Inc., Rancho Dominguez, Calif.) to concentrate and separate small molecules, yielding 6.4 g of the low molecular weight fraction and 2.8 g of the high molecular weight fraction.

A tropoelastin promoter assay was conducted on different samples of water extracts of *Phyllanthus niruri* (i.e., the high molecular weight fraction and the low molecular weight fraction as prepared above, and a water extract containing all molecular weight species that had not been subjected to fractionation).

Specifically, rat cardiac myoblasts H9C2 cells were purchased from ATCC (Manassas, Va.). Cultures were maintained in Dulbecco's modified Eagle's medium (DMEM from Invitrogen Life Technologies, Carlsbad, Calif.) supplemented with 10% fetal bovine serum, 100 units/ml penicillin, and 50 ug/ml streptomycin (Invitrogen life technologies, Carlsbad, Calif.).

Cell cultures were transiently transfected with the elastin promoter-luciferase reporter construct (Elp2.2—a 2.2 kb Elastin promoter fragment from nt −2267 to nt +2), driving the firefly luciferase gene, which was obtained from Promega (Madison, Wis.). In all transfections, a construct with the thymidine kinase promoter and the Renilla luciferase reporter gene (pRL-TK, Promega, Madison, Wis.) was included as an internal control.

Cells grown in 48-well plates were transfected with 0.45 ug total DNA per well using Lipofectamine 2000 (Invitrogen life technologies, Carlsbad, Calif.). One day after transfection, cells were treated with the water extracts of *Phyllanthus niruri* (whole, high molecular weight fraction, or low molecular weight fraction) at multiple concentrations for approximately 24 hours before they were lysed for luciferase assays, using Dual-Luciferase Reporter System from Promega (Madison, Wis.), following manufacturer's protocol. The firefly luciferase activity was measured first (representing elastin promoter activity), followed by the renilla luciferase (internal control), using luminometer LMAX, from Molecular Devices (Sunnyvale, Calif.). The ratio of these two luciferase activities (RLU) was used to evaluate the activity of each sample.

Prior to subjecting to the tropoelastin promoter assay, each water extract was dissolved in DMSO-Water (50:50) at a stock concentration of 1.0 mg/mL, and was diluted into tissue culture media containing 2% serum from that stock.

The results are shown below in Table 3.

TABLE 3

| Sample | Concentration (on active basis) | Increase in Tropoelastin Promoter Activity Over Control |
|---|---|---|
| *Phyllanthus niruri* (whole) | 0.1 ug/mL | 1.22 ± 0.19** |
| Water Extract, not fractionated | 0.025 ug/mL | 1.85 ± 0.54* |
| Water Extract, High Molecular Weight Fraction | 0.025 ug/mL | 1.97 ± 0.46** |
| Water Extract, Low Molecular Weight Fraction | 0.025 ug/mL | 2.35 ± 0.27* |
| Vehicle Control (DMSO) | 0.0025% | 1.00 ± 0.43 |

*= $P < 0.05$ using a Student's t-Test
**= $P < 0.1$ using a Student's t-Test

The low molecular weight fraction of the *Phyllanthus niruri* water extract resulted in a substantial increase tropoelastin promotion compared to the *Phyllanthus niruri* water extract containing both high and low molecular weight species. Tropoelastin promotion was 27% higher for the low molecular weight fraction (2.35) compared to the water extract containing all molecular weight species (1.85).

Example V

A collagen promoter assay was conducted as follows on the samples of water extracts of *Phyllanthus niruri* described in Example III (i.e., a high molecular weight fraction, a low molecular weight fraction, and a water extract containing the full range of molecular weight species).

Rat cardiac myoblasts H9C2 cells were purchased from ATCC (Manassas, Va.). Cultures were maintained in Dulbecco's modified Eagle's medium (DMEM from Invitrogen Life Technologies, Carlsbad, Calif.) supplemented with 10% fetal bovine serum, 100 units/ml penicillin, and 50 ug/ml streptomycin (Invitrogen life technologies, Carlsbad, Calif.).

Cell cultures were transiently transfected with the Collagen1A promoter-luciferase reporter construct, driving the firefly luciferase gene, which was obtained from PREMAS Biotech Pvt. Ltd (Haryana, India). In all transfections, a construct with the thymidine kinase promoter and the Renilla luciferase reporter gene (pRL-TK, Promega, Madison, Wis.) was included as an internal control.

Cells grown in 48-well plates were transfected with 0.45 ug total DNA per well using Lipofectamine 2000 (Invitrogen life technologies, Carlsbad, Calif.). One day after transfection, cells were treated with *Phyllanthus niruri* (whole or high or low molecular weight fractions) at multiple concentrations for approximately 24 hours before they were lysed for luciferase assays, using Dual-Luciferase Reporter System from Promega (Madison, Wis.), following manufacturer's protocol. The firefly luciferase activity was measured first (representing collagen promoter activity), followed by the renilla luciferase (internal control), using luminometer LMAX, from Molecular Devices (Sunnyvale, Calif.). The ratio of these two luciferase activities (RLU) was used to evaluate the activity of each promoter.

Prior to subjecting to the collagen promoter assay, each water extract was dissolved in DMSO-Water (50:50) at a stock concentration of 1.0 mg/mL, and was diluted into tissue culture media containing 2% serum from that stock.

The results are shown below in Table 4.

TABLE 4

| Sample | Concentration (on active basis) | Increase in Collagen1A Promoter Activity Over Control |
|---|---|---|
| *Phyllanthus niruri* (whole) | 0.5 ug/mL | 1.27 ± 0.29** |
| Water Extract | 0.5 ug/mL | 1.51 ± 0.12** |
| Water Extract, High Molecular Weight Fraction | 0.5 ug/mL | 1.55 ± 0.15** |
| Water Extract, Low Molecular Weight Fraction | 0.5 ug/mL | 2.03 ± 0.12* |
| Vehicle Control (DMSO) | 0.05% | 1.00 ± 0.13 |

\* = $P < 0.05$ using a Student's t-Test
\*\* = $P < 0.1$ using a Student's t-Test The low molecular weight fraction of the *Phyllanthus niruri* water extract resulted in a substantial increase in collagen promotion compared to the *Phyllanthus niruri* water extract containing the full range of molecular weights. Specifically, collagen promotion provided by the low molecular weight fraction (2.03) was 34% higher compared to that provided by the water extract containing both high and low molecular weight species (1.51).

Moreover, this data shows that the high molecular weight fraction actually inhibits the efficacy of the low molecular weight fraction. The low molecular weight fraction constituted approximately 69.6% by weight (6.4 g) of the total *Phyllanthus niruri* water extract. The high molecular weight fraction was approximately 30.4% by weight of the total *Phyllanthus niruri* water extract (2.8 g) Accordingly, the expected collagen promotion for the entire water extract would be (0.696×2.03)+(0.304×1.55), or 1.88. However, the actual collagen promotion provided by the unfractionated water extract was 1.51, approximately 20% lower than the expected value. This discrepancy suggests that the high molecular weight fraction inhibits the efficacy of the low molecular weight fraction.

Example VI

The effect of low molecular weight (LMW) fractions of *Phyllanthus niruri* was evaluated for topical anti-inflammatory activity on human epidermal equivalents. Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm$^2$) with the low molecular weight (LMW) fractions of *Phyllanthus niruri* dissolved in media before exposure to solar ultraviolet light (1000 W-Oriel solar simulator equipped with a 1-mm Schott WG 320 filter; UV dose applied: 70 kJ/m$^2$ as measured at 360 nm). Equivalents were incubated for 24 hours at 37° C. with maintenance medium then supernatants were analyzed for IL-8 and IL-1α cytokine release using commercially available kits (Millipore Corp., Billerica, Mass.). IL-8 release and percentage inhibition of skin inflammation are shown in Table 5, below. Similarly, results for IL-1 are shown in Table 6, below.

TABLE 5

| Treatment (Dose, as % w/v) | Mean of IL-8 Release (pg/mL) | Percent Inhibition of Skin Inflammation |
|---|---|---|
| Untreated, No UV | 263.77 | — |
| UV (60 KJ) | 483.67 | — |
| UV (60 KJ) + LMW *Phyllanthus niruri* extract 0.1% | 357.35 | 26.12% |
| UV (60 KJ) + LMW *Phyllanthus niruri* 1% | 213.93 | 55.77% |
| UV (60 KJ) + LMW *Phyllanthus niruri* 2% | 119.14 | 75.37% |
| UV (60 KJ) + LMW *Phyllanthus niruri* 5% | 227.11 | 53.04% |

TABLE 6

| Treatment (Dose, as % w/v) | Mean of IL-1α Release (pg/mL) | Percent Inhibition of Skin Inflammation |
|---|---|---|
| Untreated, No UV | 29.92 | — |
| UV (60 KJ) | 227.56 | — |
| UV (60 KJ) + LMW *Phyllanthus niruri* extract 0.1% | 218.36 | 4.04 |
| UV (60 KJ) + LMW *Phyllanthus niruri* 1% | 41.82 | 81.62 |
| UV (60 KJ) + LMW *Phyllanthus niruri* 2% | 32.84 | 85.57 |
| UV (60 KJ) + LMW *Phyllanthus niruri* 5% | 73.76 | 67.59 |

Based on these results, it can be concluded that application of the inventive *Phyllanthus niruri* extract was able to significantly reduce the UV-stimulated release of inflammatory mediators. Therefore, *Phyllanthus niruri* extracts would be expected to provide an effective anti-inflammatory benefit when applied to skin.

Example VII

UV-induced hydrogen peroxide formation was determined using a modification of the method of Martin et al, *Arch Dermatol Res*. (2008) 300:69-80, in reconstituted epidermis and the human epithelial cell line, KB. Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. After 24 hours, the tissues were incubated for 30 minutes with 5 μM of the hydrogen peroxide-sensitive fluorescent probe 5-(and-6)-chloromethyl-2',7'-dichlorodihydro-fluorescein diacetate, acetyl ester (CM-H2DCFDA) (Invitrogen Corp., Carlsbad, Calif.). After incubation, the plate was rinsed to remove excess probe and equivalents were topically treated (2 mg/cm$^2$) with low molecular weight water soluble *Phyllanthus niruri* extract dissolved in media. The plate was immediately read on a fluorescent plate reader set at wavelengths 485 nm excitation/530 nm emission to detect basal peroxide formation. The plate was then exposed to UV (1000 W-Oriel solar simulator equipped with a 1 mm Schott WG 320 filter; UV dose applied 4.2 kJ/m$^2$ as measured at 360 nm). The plate was read 60 minutes post UV exposure. Fluoroescence and percent inhibition of UV-induced ROS are shown in Table 7, below.

TABLE 7

| Treatment (Dose, as % w/v) | Mean Fluorescent Units | Percent Inhibition of UV-induced ROS Production |
|---|---|---|
| Untreated, No UV | 32.20 | — |
| UV (60 KJ) | 419.82 | — |
| UV (60 KJ) + LMW Phyllanthus niruri extract 0.1% | 213.71 | 49.10 |
| UV (60 KJ) + LMW Phyllanthus niruri 1% | 112.71 | 73.15 |
| UV (60 KJ) + LMW Phyllanthus niruri 2% | 102.71 | 75.53 |
| UV (60 KJ) + LMW Phyllanthus niruri 5% | 27.59 | 93.43 |

Based on these results, it can be concluded that the application of low molecular weight (LMW) fractions of Phyllanthus niruri was able to significantly reduce the UV-stimulated production of ROS in reconstituted epidermis. Therefore when applied to skin, Phyllanthus niruri extracts would be expected to provide protection against induction of ROS from solar irradiation.

Example VIII

KB cells obtained from ATCC (ATCC#CCL-17, Manassas, Va.) were plated in 96-well tissue culture treated plates at a density of 5000 cells/well in Dulbecco's modified Eagle's medium (DMEM) supplemented with 10% fetal bovine serum (Invitrogen Corp., San Diego, Calif.). After 48 hours, cells were incubated for 30 minutes with 5 µM of the hydrogen peroxide-sensitive fluorescent probe 5-(and-6)-chloromethyl-2',7'-dichlorodihydro-fluorescein diacetate, acetyl ester (CM-H2DCFDA) (Invitrogen Corp., Carlsbad, Calif.). After incubation, the plate was rinsed to remove excess probe and low molecular weight water soluble Phyllanthus niruri extract was added at the indicated concentrations. The plate was immediately read on a fluorescent plate reader set at wavelengths 485 nm excitation/530 nm emission to detect basal peroxide formation. The plate was then exposed to UV (1000 W-Oriel solar simulator equipped with a 1 mm Schott WG 320 filter; UV dose applied 4.2 kJ/m² as measured at 360 nm). The plate was read 60 minutes post UV exposure.

Fluoroescence and percent inhibition of UV-induced ROS are shown in Table 8, below.

TABLE 8

| Treatment (Dose, as % w/v) | Mean Fluorescent Units | Percent Inhibition of UV-induced ROS Production |
|---|---|---|
| untreated | 77.43 | — |
| UV treated | 249.69 | — |
| UV + LMW Phyllanthus niruri (0.0001%) | 226.37 | 9.34% |
| UV + LMW Phyllanthus niruri (0.001%) | 210.95 | 15.51% |
| UV + LMW Phyllanthus niruri (0.01%) | 169.02 | 32.31% |
| UV + LMW Phyllanthus niruri (0.1%) | 63.76 | 74.47% |

Based on these results, it can be concluded that the application of low molecular weight (LMW) fractions of Phyllanthus niruri was able to significantly reduce the UV-stimulated production of ROS in human epithelial cells. Therefore when applied to skin, Phyllanthus niruri extracts would be expected to provide protection against induction of ROS from solar irradiation.

Example IX

Skin epidermal equivalent tissues are available commercially from MatTek's MelanoDerm™ System and were used for the following tests. MatTek's MelanoDerm™ System consists of normal, human-derived epidermal keratinocytes (NHEK) and melanocytes (NHM) which have been cultured to form a multilayered, highly differentiated model of the human epidermis. Specifically, MEL-300-B tissues, each 9 mm in diameter were used in the following tests.

The test materials prepared in an appropriate vehicle (water)) and tested concentrations were applied topically to the skin model daily and the experiment lasted for 8 days. Measurement was taken on day 9.

The macroscopic and microscopic visual tissue darkening end points were measured by taking pictures with a digital camera. The Degree of Lightness for each tissue (L-Value) was measured using a spectrophotometer (Konica Minolta CM-2600d). The ΔL (degree of lightness as compared to control) for each test sample is calculated as per following formula:

$$\Delta L = L\text{-value of treated sample} - L\text{-value of control sample.}$$

Results from the skin lightening test are shown below in Table 9.

TABLE 9

| Extract Code | Conc. (%) | Degree of Lightness (ΔL) | Std. Dev. |
|---|---|---|---|
| LMW Phyllanthus niruri extract | 0.1% | −0.41 | 0.42 |
| LMW Phyllanthus niruri extract | 0.5% | 0.96 | 0.31 |
| LMW Phyllanthus niruri extract | 1% | 2.51 | 0.42 |

Example X

Topical formulations according to the invention were made using the ingredients shown in Table 10 and Table 11.

TABLE 10

| INCI Name | Trade Name | Percentage |
|---|---|---|
| WATER | PURIFIED WATER | 71.59 |
| Xanthan Gum | Keltrol CG | 0.16 |
| Edetate Disodium | Versene NA | 0.15 |
| White Petrolatum | Perfecta | 5 |
| Medium Chain Triglyceride | Labrafac CC | 0.75 |
| Glycerin | GLYCEROL | 5.50 |
| Ricinus Communis Seed Oil | Castor Oil | 1.8 |
| Cetyl Alcohol, NF | Lanette 16 | 2.2 |
| Emulsifying Wax, NF | PolaWax, NF | 1.5 |
| Cocoa Butter | Cocoa Butter, NF | 2 |
| Glyceryl Stearate SE | Glyceryl Stearate SE | 3.00 |
| Glyceryl Stearate/PEG 100 Stearate | Lexemul 561 | 5.00 |
| Diazolidinyl Urea | Germall II | 0.25 |
| Low Molecular Weight Fraction of Water Extract of Phyllanthus niruri from Example 1 | | 1.00 |
| Iodopropynyl Butylcarbonate | Glycacil L | 0.1 |

This topical formulation was made as follows.

Water Phase
  Step 1. Purified Water was charged into the main container at a temperature of 20-40° C.
  Step 2. Xanthan Gum NF was added to the main container. A 30 mesh screen may be used if lumpy.
  Step 3. The wall of the main container was rinsed with Purified Water to remove any Xanthan Gum from the walls.
  Step 4. The batch was mixed for 15-25 minutes. Hydration of the gum was checked.
  Step 5. Glycerin USP Special and Edetate Disodium USP were added.
  Step 6. The batch was heated to 65° C. (63-67° C.) while mixing.

Oil Phase
  Step 1. Into a clean suitable phase container, the following chemicals were added in this order: Medium Chain Triglycerides, Castor Oil, Cocoa Butter, and Premelted Petrolatum USP.
  Step 2. The oil phase temperature was set at 65° C. (63-67° C.) and mixing at medium speed was started.
  Step 3. While heating the batch to 65° C., the following chemicals were added in this order, allowing each to dissolve before adding the next: Glyceryl Stearate SE, Cetyl Alcohol, Emulsifying Wax, and Glyceryl Stearate.
  Step 4. When the temperature reached 65° C. (63-67° C.), the ingredients were mixed for 15-25 minutes.

Phasing of the Batch, Main Container
  Step 1. When both phases were homogenous and at a temperature of 63-67° C., the oil phase was transferred to the water phase while mixing the water phase at medium speed.
  Step 2. When transfer was completed, the oil phase tank was rinsed with Purified Water. The rinsings were heated to 63-67° C. and added to the main container.
  Step 3. The batch was mixed for 10-20 minutes.
  Step 4. The batch was cooled to 40° C. (38-42° C.).
  Step 5. When temperature was 48-50° C. the mixing speed was increased to medium-high.
  Step 6. *Phyllanthus niruri* (1% active) was added.
  Step 7. When the temperature was at 44° C. or lower, the Diazolidinyl Urea Premix was added.
  Step 8. Iodopropyl Butylcarbamate was added.
  Step 9. The batch was mixed for 5-10 minutes.
  Step 10. If required, the batch was QS'd with Purified Water.
  Step 11. Mixing was continued and cooling of the batch to 32-34° C. was begun.
  Step 12. When the batch reached 33° C. (32-34° C.), mixing and cooling were ended.

Diazolidinyl Urea (Germall II) Premix
  Step 1. Purified water was added into a stainless steel premix tank.
  Step 2. Diazolidinyl Urea was added with mixing.
  Step 3. The ingredients were mixed for an additional 10-20 minutes to dissolve completely.
  Step 4. The premix was held for addition to the batch.

TABLE 11

| INCI Name | Trade Name | Percentage |
| --- | --- | --- |
| Water | Purified Water | 55.79 |
| DISODIUM EDTA | EDTA BD | 0.20 |
| Acrylates C10-30 Alkyl Acrylate | Pemulen TR-1 | 0.25 |
| Potassium Cetyl Phosphate | Amphisol K | 1.00 |
| Sodium Hydroxide | Sodium Hydroxide | 0.52 |
| Phenylbenzimidazole Sulfonic Acid | Eusolex 232 | 2.00 |
| Methylene Bis-Benzotriazolyl Tetramethylbutylphenol | Tinosorb M | 1.00 |
| ETHYLHEXYL SALICYLATE | Neoheliopan OS | 3.00 |
| OCTOCRYLENE | Neoheliopan 303 | 2.00 |
| BENZOPHENONE-3 | Uvinul M40 | 0.50 |
| Ethylhexyl Triazone | Uvinul T 150 | 3.00 |
| AVOBENZONE | Parsol 1789 | 2.00 |
| HOMOSALATE | Neo Heliopan HMS | 5.00 |
| Bis-Ethylhexyloxyphenol Methoxyphenyl Triazine | Tinosorb S | 1.00 |
| DIETHYLHEXYL 2,6-NAPHTHALATE | Corapan TQ | 0.01 |
| C12-15 Alkyl Benzoate | Tegosoft TN | 10.00 |
| Cetyl Alcohol | Lanette C16 98-100 MY | 2.50 |
| Glyceryl Stearate and PEG-100 Stearate | Arlacel 165 FL | 2.40 |
| Ethylhexylglycerin | Sensiva SC 50 | 0.50 |
| BHT | Ionol CP | 0.07 |
| Dimethicone/Vinyl Dimethicone Crosspolymer; Silica | Dow Corning 9701 Cosmetic Powder | 0.50 |
| Dimethicone; Tetra Silane | DC 593 | 1.50 |
| SILICA | Spheron L 1500 | 1.00 |
| Dimethicone | DC 200 350 cps | 2.00 |
| Dimethicone; Dimethiconol | DC1403 | 1.00 |
| Fragrance | Fragrance | 0.08 |
| Low Molecular Weight Fraction of Water Extract of *Phyllanthus niruri*, Inventive Example, Ex. 1 | | 1.00 |
| Methylisothiazolinone; Polyaminopropyl Biguanide | Micrcare MTB | 0.18 |

This topical formulation was prepared as follows:

Water Phase
  Step 1. Water was added into main mixing container and mixing was started.
  Step 2. EDTA BD was added and mixed until dissolved.
  Step 3. Mixing speed was increased and Pemulen TR-1 was added. The ingredients were mixed until fully dispersed (30 min).
  Step 4. Eusoulex was premixed with Water; an NaOH solution was added to the water phase.
  Step 5. Mixing was continued and Amphisol K was added and mixed for 20 min. Heating to 80° C.-85° C. was begun.
  Step 6. The temperature was maintained between 80° C.-85° C. until ready for phasing.

Oil Phase
  Step 1. Into a premix container, the following were added one by one and mixed
    Neo Heliopan OS
    Tegosoft TN
    Neo Heliopan 303
    Uvinul M40
    Parsol 1789
    Neo Heliopan HMS
    Corapan TQ
    Lanette C16 98-100 MY
    Arlacel 165 FL
    Sensiva SC-50
    Ionol CP
    Dow Corning 9701 Cosmetic Powder.
  Step 2. The mixture was heated to 85° C.-90° C. with continued mixing.

Phasing
  Step 1. When both phases were between 80° C.-85° C., the oil phase was added to the water phase under homogenization and homogenized for 10 min.

Step 2. The ingredients were cooled to 70° C.-75° C. and Sodium Hydroxide 10% Solution was added and mixed until uniform.

Step 3. When the temperature was below 75° C., Tinosorb M and Tinosorb S were added and mixed for 10 mins. When the temperature was below 45-50 C, Spheron L-1500, dimethicone, DC 1403, and fragrance were added and mixed until uniform.

Step 4. The ingredients were cooled to a temperature of 35° C.-40° C.

Step 5. Microcare MTB was added and mixed until uniform.

Step 6. *Phyllanthus niruri* (1% active) was added and mixed until uniform.

Step 7. The ingredients were homogenized for 5 minutes.

The topical formulations shown in Tables 10 and 11 were put in 50° C. oven for 1 week and showed primary good stability.

We claim:

1. A method of lightening skin comprising the step of applying to skin in need of skin lightening treatment a topical formulation comprising a cosmetically acceptable topical carrier and an effective amount of a low molecular weight fraction of *Phyllanthus niruri* substantially free of molecular species having a molecular weight of greater than about 100,000 daltons.

2. The method of claim 1, wherein said low molecular weight fraction contains less than about 5% by weight of molecular species having a molecular weight greater than about 100,000 daltons.

3. The method of claim 1, wherein said low molecular weight fraction is water extractable from *Phyllanthus niruri*.

4. The method of claim 1, wherein said topical formulation comprises about 0.1 to about 5% by weight of said low molecular weight fraction.

5. The method of claim 1, wherein said topical formulation comprises an additional skin lightening agent selected from the group consisting of phenylethyl resorcinol, 4-hexyl resorcinol, α-arbutin, kojic acid, nivitol, ascorbyl-2-glucoside, soy extract, niacinamide, and combinations thereof.

* * * * *